(12) United States Patent
Butts et al.

(10) Patent No.: US 10,737,033 B2
(45) Date of Patent: Aug. 11, 2020

(54) PARTIALLY LUBRICATED SYRINGE BARRELS, PLUNGERS, AND SEAL MEMBERS AND RELATED METHODS

(71) Applicant: Merit Medical Systems, Inc., South Jordan, UT (US)

(72) Inventors: David Butts, Riverton, UT (US); Richard Jenkins, Bluffdale, UT (US); Gregory R. McArthur, Sandy, UT (US)

(73) Assignee: Merit Medical Systems, Inc., South Jordan, UT (US)

( * ) Notice: Subject to any disclaimer, the term of this patent is extended or adjusted under 35 U.S.C. 154(b) by 0 days.

(21) Appl. No.: 15/410,364

(22) Filed: Jan. 19, 2017

(65) Prior Publication Data
US 2017/0209646 A1  Jul. 27, 2017

Related U.S. Application Data

(60) Provisional application No. 62/281,569, filed on Jan. 21, 2016.

(51) Int. Cl.
*A61M 5/31* (2006.01)
*A61M 5/315* (2006.01)

(52) U.S. Cl.
CPC ...... *A61M 5/3134* (2013.01); *A61M 5/31513* (2013.01); *A61M 2005/3131* (2013.01); *A61M 2005/3142* (2013.01)

(58) Field of Classification Search
CPC ........ A61M 2005/3131; A61M 5/3134; A61M 5/31513; A61M 5/3129; A61M 5/3135; A61M 5/3205
See application file for complete search history.

(56) References Cited

U.S. PATENT DOCUMENTS

| 4,439,184 A | * | 3/1984 | Wheeler | A61M 3/005 604/191 |
| 4,500,310 A | * | 2/1985 | Christinger | A61M 5/31513 604/228 |
| 4,986,820 A | * | 1/1991 | Fischer | A61M 5/31511 604/218 |

(Continued)

FOREIGN PATENT DOCUMENTS

| EP | 0338671 | 10/1989 |
| EP | 0375778 | 7/1990 |

(Continued)

OTHER PUBLICATIONS

Office Action dated Sep. 4, 2018 for U.S. Appl. No. 15/410,305.
(Continued)

*Primary Examiner* — Nathan R Price
*Assistant Examiner* — Mark A Igel
(74) *Attorney, Agent, or Firm* — Stoel Rives LLP (57) ABSTRACT

Syringe systems including barrels having lubricated portions and non-lubricated portions are provided. The non-lubricated portions may be configured to be loaded with injectable materials, such as embolic agents. The injectable materials may comprise polyvinyl alcohol. Also provided are methods of lubricating portions of barrels of syringe systems with lubricants including silicone or silicone-free lubricants.

12 Claims, 8 Drawing Sheets

(56) References Cited

U.S. PATENT DOCUMENTS

| | | | | |
|---|---|---|---|---|
| 4,997,423 A * | 3/1991 | Okuda | A61M 5/2429 | 604/218 |
| 5,009,646 A * | 4/1991 | Sudo | A61M 5/31513 | 604/230 |
| 5,314,416 A | 5/1994 | Lewis | | |
| 5,338,312 A * | 8/1994 | Montgomery | A61M 5/3129 | 427/2.3 |
| 5,397,313 A | 3/1995 | Gross | | |
| 5,411,488 A | 5/1995 | Pagay et al. | | |
| 5,735,825 A * | 4/1998 | Stevens | A61M 5/31513 | 604/218 |
| 6,296,893 B2 * | 10/2001 | Heinz | A61L 29/085 | 427/2.28 |
| 6,586,039 B2 * | 7/2003 | Heinz | A61M 5/3129 | 427/2.1 |
| 6,663,603 B1 | 12/2003 | Guyre et al. | | |
| 7,186,242 B2 * | 3/2007 | Gyure | A61M 5/31513 | 604/230 |
| 7,927,315 B2 * | 4/2011 | Sudo | A61M 5/31511 | 604/218 |
| 8,475,415 B2 | 7/2013 | Schiller | | |
| 8,740,856 B2 * | 6/2014 | Quinn | A61M 5/31511 | 604/218 |
| 9,592,346 B2 * | 3/2017 | Quinn | A61M 5/31511 | |
| 10,183,118 B2 * | 1/2019 | Quinn | A61M 5/31513 | |
| 2001/0004466 A1 * | 6/2001 | Heinz | A61L 29/085 | 427/2.1 |
| 2002/0198500 A1 * | 12/2002 | Leung | A61M 5/508 | 604/231 |
| 2004/0122376 A1 * | 6/2004 | Gyure | A61M 5/31513 | 604/230 |
| 2004/0138612 A1 * | 7/2004 | Shermer | A61M 5/142 | 604/93.01 |
| 2005/0137533 A1 | 6/2005 | Sudo et al. | | |
| 2006/0178643 A1 * | 8/2006 | Sudo | A61M 5/31511 | 604/230 |
| 2007/0219508 A1 | 9/2007 | Bisegna | | |
| 2011/0034882 A1 * | 2/2011 | Quinn | A61M 5/31513 | 604/218 |
| 2011/0178475 A1 * | 7/2011 | Tanaka | A61M 5/31511 | 604/222 |
| 2012/0136298 A1 | 5/2012 | Bendix et al. | | |
| 2014/0031764 A1 * | 1/2014 | Abe | A61L 29/085 | 604/221 |
| 2014/0062036 A1 * | 3/2014 | Maeda | A61M 5/31511 | 277/615 |
| 2014/0207081 A1 * | 7/2014 | Quinn | A61M 5/31511 | 604/222 |
| 2015/0018800 A1 * | 1/2015 | Reb | A61M 5/3129 | 604/507 |
| 2016/0243305 A1 | 8/2016 | Nakamura | | |
| 2017/0312177 A1 | 11/2017 | Bhargava et al. | | |

FOREIGN PATENT DOCUMENTS

| | | |
|---|---|---|
| WO | 2004044464 | 5/2004 |
| WO | 2015006444 | 1/2015 |

OTHER PUBLICATIONS

International Search Report and Written Opinion dated May 1, 2017 for PCT/US2017/014117.
International Search Report and Written Opinion dated May 22, 2017 for PCT/US2017/014043.
Office Action dated Feb. 8, 2019 for U.S. Appl. No. 15/410,305.
European Search Report dated Aug. 26, 2019 for EP17741885.2.
Office Action dated Jul. 9, 2019 for U.S. Appl. No. 15/410,305.
Notice of Allowance dated Feb. 14, 2020 for U.S. Appl. No. 15/410,305.

* cited by examiner

PARTIALLY LUBRICATED SYRINGE BARRELS, PLUNGERS, AND SEAL MEMBERS AND RELATED METHODS

RELATED APPLICATIONS

This application claims priority to U.S. Provisional Application No. 62/281,569, filed on Jan. 21, 2016 and titled, "PARTIALLY LUBRICATED SYRINGE BARRELS, PLUNGERS, AND SEAL MEMBERS AND RELATED METHODS" which is hereby incorporated by reference in its entirety.

TECHNICAL FIELD

The present disclosure relates generally to syringe systems comprising barrels including lubricated portions and non-lubricated portions. More specifically, the present disclosure relates to barrels including non-lubricated portions configured to be loaded with injectable materials and methods of lubricating portions of the barrels. This disclosure also relates to various embodiments of syringe seal members, including seal members configured to interact with lubricants on a syringe barrel. Related methods are also disclosed.

BRIEF DESCRIPTION OF THE DRAWINGS

The embodiments disclosed herein will become more fully apparent from the following description and appended claims, taken in conjunction with the accompanying drawings. While various aspects of the embodiments are presented in drawings, the drawings depict only typical embodiments, which will be described with additional specificity and detail through use of the accompanying drawings in which:

2

DETAILED DESCRIPTION

The various embodiments disclosed herein generally relate to syringe systems comprising barrels including lubricated portions and non-lubricated portions. In some embodiments, the non-lubricated portions are configured to be loaded with injectable materials. In certain embodiments, the injectable materials may comprise polyvinyl alcohol (PVA). In various embodiments, the injectable materials may comprise a substance including gelatin foam (e.g., GELFOAM®). Also disclosed herein are methods of lubricating portions of barrels of syringe systems.

It will be appreciated that various features are sometimes grouped together in a single embodiment, figure, or description thereof for the purpose of streamlining the disclosure. Many of these features may be used alone and/or in combination with one another.

Embodiments may be understood by reference to the drawings, wherein like parts are designated by like numerals throughout. It will be readily understood that the components of the present disclosure, as generally described and illustrated in the drawings herein, could be arranged and designed in a wide variety of different configurations. Thus, the following more detailed description of the embodiments of the apparatus is not intended to limit the scope of the disclosure, but is merely representative of possible embodiments of the disclosure. In some cases, well-known structures, materials, or operations are not shown or described in detail. While the various aspects of the embodiments are presented in drawings, the drawings are not necessarily drawn to scale unless specifically indicated.

The phrases "connected to," "coupled to," and "in communication with" refer to any form of interaction between two or more entities, including but not limited to mechanical, electrical, magnetic, electromagnetic, fluid, and thermal interaction. Two components may be coupled to each other even though they are not in direct contact with each other. For example, two components may be coupled to each other through an intermediate component.

The terms "proximal" and "distal" refer to opposite ends of a medical device, including the devices disclosed herein. As used herein, the proximal portion of a medical device is the portion nearest a practitioner during use, while the distal portion is the portion at the opposite end. For example, the proximal end of a syringe system is defined as the end closest to the practitioner during utilization of the syringe system. The distal end is the end opposite the proximal end, along the longitudinal direction of the syringe system.

The term "silicone" refers to polymers that include repeating units of siloxane (e.g., poly-siloxane (($R_2SiO)_n$)). As used herein, the terms silicone and poly-siloxane may be used interchangeably.

The term "shelf stable" refers to syringe systems, wherein any components of the syringe system, the injection material, and/or an interaction between the injection material and the syringe system (i.e., an interaction in a pre-loaded syringe system) are such that after a given timeframe (e.g., six months, one year, two years, three years, etc.) the syringe system and the injection material are still suitable for their intended purpose. For example, when the injection material comprises an embolic agent (e.g., a microparticle or a microsphere), agglomeration of the embolic agent may render the pre-loaded syringe system unsuitable for its intended purpose. For example, agglomeration of more than about 10% of the embolic agent may render the pre-loaded syringe unsuitable for its intended purpose. Likewise, adhesion of the injection material to one or more components of the syringe system (e.g., a barrel) may render the pre-loaded syringe unsuitable for its intended purpose.

The term "sterilization compatible" refers to components or materials configured to be sterilized without rendering the components or materials unsuitable for their intended purpose. If a component or material is configured for sterilization by at least one method of sterilization without being rendered unsuitable for its intended purpose, then the material is "sterilization compatible." For example, a polymeric barrel may deform when autoclaved at temperatures sufficient to sterilize the barrel, rendering the barrel unsuitable for maintaining a seal with a seal member of a plunger. However, if the same polymeric barrel may be sterilized by another sterilization technique (e.g., by irradiation) and maintain suitability for its intended purpose, then the polymeric material is "sterilization compatible."

The term "irradiation compatible" refers to components or materials configured to be sterilized by irradiation without rendering the components or materials unsuitable for their intended purpose. For example, a plunger or an interior surface of a barrel may comprise a material (e.g., a lubricant) that upon irradiation changes in physical properties such that the syringe is unsuitable for its intended purpose. For example, irradiation may alter certain materials such that a syringe using those materials would have an unacceptably high initial peak force required to start movement of a plunger. Or, in another example, irradiation may alter certain materials such that a syringe using those materials would have an unacceptably non-uniform force required for travel of the plunger over the length of the barrel or an unacceptably high force required for travel of the plunger over the length of the barrel.

Figure 1:
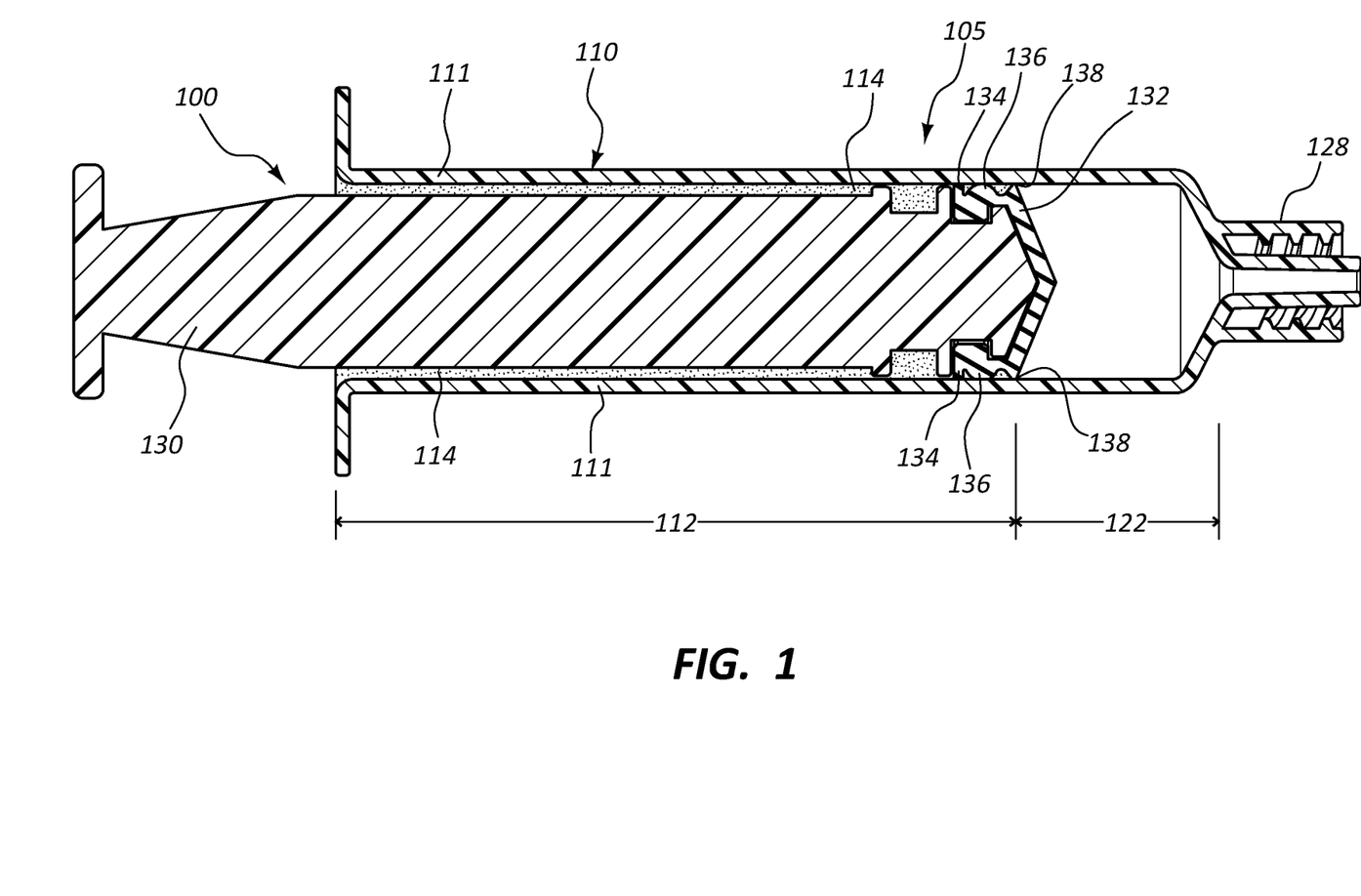
FIG. 1 is a cross-sectional side view of an embodiment of a syringe system.

FIG. 1 is a cross-sectional side view of an embodiment of a syringe system 100. As depicted, the syringe system 100 can comprise a syringe body 105 and a plunger 130. In some embodiments, the plunger 130 may be configured to be disposed and/or displaceable within at least a portion of a barrel 110 of the syringe body 105. The syringe system 100 can also comprise an inlet/outlet port 128 disposed at a distal end of the syringe body 105.

As shown, the plunger 130 can comprise a seal member 132. As shown, the seal member 132 can comprise a proximal ridge 134, or sealing ring, disposed around at least a portion of a circumference of the seal member 132 at or adjacent a proximal end of the seal member 132. The seal member 132 can also comprise a distal ridge 138 disposed around at least a portion of the circumference of the seal member 132 at or adjacent the distal end of the seal member 132. Stated another way, the distal ridge 138 may be disposed distal of the proximal ridge 134. The seal member 132 can further comprise a medial ridge 136 disposed around at least a portion of the circumference of the seal member 132 at a position between each of the proximal ridge 134 and the distal ridge 138. In certain embodiments, the seal member 132 may comprise one ridge, two ridges, three ridges, four ridges, five ridges, six ridges, or another suitable number of ridges.

In some embodiments, the seal member 132 may be integrally molded with the plunger 130. In some other embodiments, the seal member 132 may be a discrete component of the syringe system 100 and the seal member 132 may be coupled to the plunger 130 (e.g., to a distal end of the plunger 130). The seal member 132 may be formed from a polymeric material. In some embodiments, the seal member 132 may be formed from silicone or poly-siloxane. In some other embodiments, the seal member 132 may be formed from a silicone-free material or poly-siloxane-free material. Seal members 132 formed from other suitable materials are also within the scope of this disclosure. Additionally, at least a portion of the seal member 132 may be lubricated. In certain embodiments, at least a portion of the seal member 132 may be lubricated with a silicone lubricant or a poly-siloxane lubricant. In certain other embodiments, at least a portion of the seal member 132 may be lubricated with a silicone-free lubricant or a poly-siloxane-free lubricant. For example, the lubricant may be a perfluoropolyether (PFPE) lubricant. Seal members 132 lubricated with other suitable lubricants are also within the scope of this disclosure.

In various embodiments, the proximal ridge 134, the medial ridge 136, and/or the distal ridge 138 may exert a radial force on an interior surface of a first wall 111 of the barrel 110. Stated another way, the proximal ridge 134, the medial ridge 136, and/or the distal ridge 138 may be configured to be compressed against the interior surface of the first wall 111 of the barrel 110. Additionally, the proximal ridge 134, the medial ridge 136, and/or the distal ridge 138 may slidably seal against the interior surface of the first wall 111 of the barrel 110. In some embodiments, the proximal ridge 134 may exert a greater radial force on the interior surface of the first wall 111 of the barrel 110 than the distal ridge 138. In certain embodiments, the medial ridge 136 may exert a greater radial force on the interior surface of the first wall 111 of the barrel 110 than the distal ridge 138. In various embodiments, each of the proximal ridge 134 and the medial ridge 136 may exert substantially equal radial forces on the interior surface of the first wall 111 of the barrel 110.

The proximal ridge 134 and/or the medial ridge 136 may be configured such that these ridges 134, 136 are compressed within the barrel 110 to form a seal between an outer surface of the seal member 132 and the inner surface of the first wall 111 of the barrel 110. In some embodiments, the compressed portions of the seal member 132 may exert a radially outward force on the inner surface of the first wall 111 of the barrel 110 and may conform to the first wall 111 of the barrel 110. This sealing force may be configured contain pressured fluids within the barrel and thus the seal member 132 may create a pressure seal when compressed within the barrel 110. In other words, in some embodiments, the proximal ridge 134 and/or the medial ridge 136 may form a pressure seal against the inner surface of the first wall 111 of the barrel 110, analogous to an O-ring, for instance.

The distal ridge 138 may be configured to form a barrier to separate materials within the system, and may not be configured as a high pressure seal. Thus, the distal ridge 138 may be understood as creating a barrier seal between the outer surface of the seal member 132 and the inner surface of the first wall 111 of the barrel 110. In some instances, the pressure seal (formed by proximal ridge 134 and/or medial ridge 136) may exert a greater force on the inner surface of the first wall 111 of the barrel 110 than the barrier seal (formed by the distal ridge 138). In some embodiments, the barrier seal formed by the distal ridge 138 may inhibit or prevent flow or migration of a lubricant from a lubricated portion 112 of the barrel 110 to a non-lubricated portion 122 of the barrel 110. The lubricated and non-lubricated portions 112, 122 of the barrel 110 are discussed in further detail below.

The radial force used to form the pressure seal may be greater than the radial force used to form the barrier seal, wherein the barrier seal inhibits, limits, or prevents flow or migration of a lubricant from the lubricated portion 112 of the barrel 110 to the non-lubricated portion 122 of the barrel 110. Other combinations of exerted radial forces are also within the scope of this disclosure. For example, the medial ridge 136 may exert a greater radial force on the interior surface of the first wall 111 of the barrel 110 than the proximal ridge 134, or vice versa.

As illustrated, the barrel 110 can comprise a lubricated portion 112 and a non-lubricated portion 122, wherein the non-lubricated portion 122 may be disposed distal of the lubricated portion 112. In some embodiments, at least a portion of the interior surface of the first wall 111 of the barrel 110 disposed in the lubricated portion 112 may be at least partially coated with a lubricant or lubricant coating 114. In some embodiments, the lubricant may be cross-linked or otherwise bonded to at least a portion of the interior surface of the first wall 111. In some other embodiments, the lubricant may not be cross-linked or otherwise bonded to the interior surface of the first wall 111. In contrast to the lubricated portion 112, at least a portion of the interior surface of the first wall 111 of the barrel 110 disposed in the non-lubricated portion 122 may lack a lubricant or lubricant coating. The lubricant 114 may aid in the displacement of the plunger 130 and the seal member 132 within at least a portion of the barrel 110 of the syringe system 100 (i.e., the lubricated portion 112). For example, the plunger 130 may be more easily displaced within the lubricated portion 112 of the barrel 110 than within the non-lubricated portion 122 of the barrel 110.

In certain embodiments, the plunger 130 may be formed from or comprise a polymeric material such as, but not limited to, an acrylonitrile-butadiene-styrene polymer, a polycarbonate, a polypropylene, a nylon, and/or a cyclo-olefin polymer or copolymer. Plungers 130 formed from other suitable materials are also within the scope of this disclosure.

Figure 2:
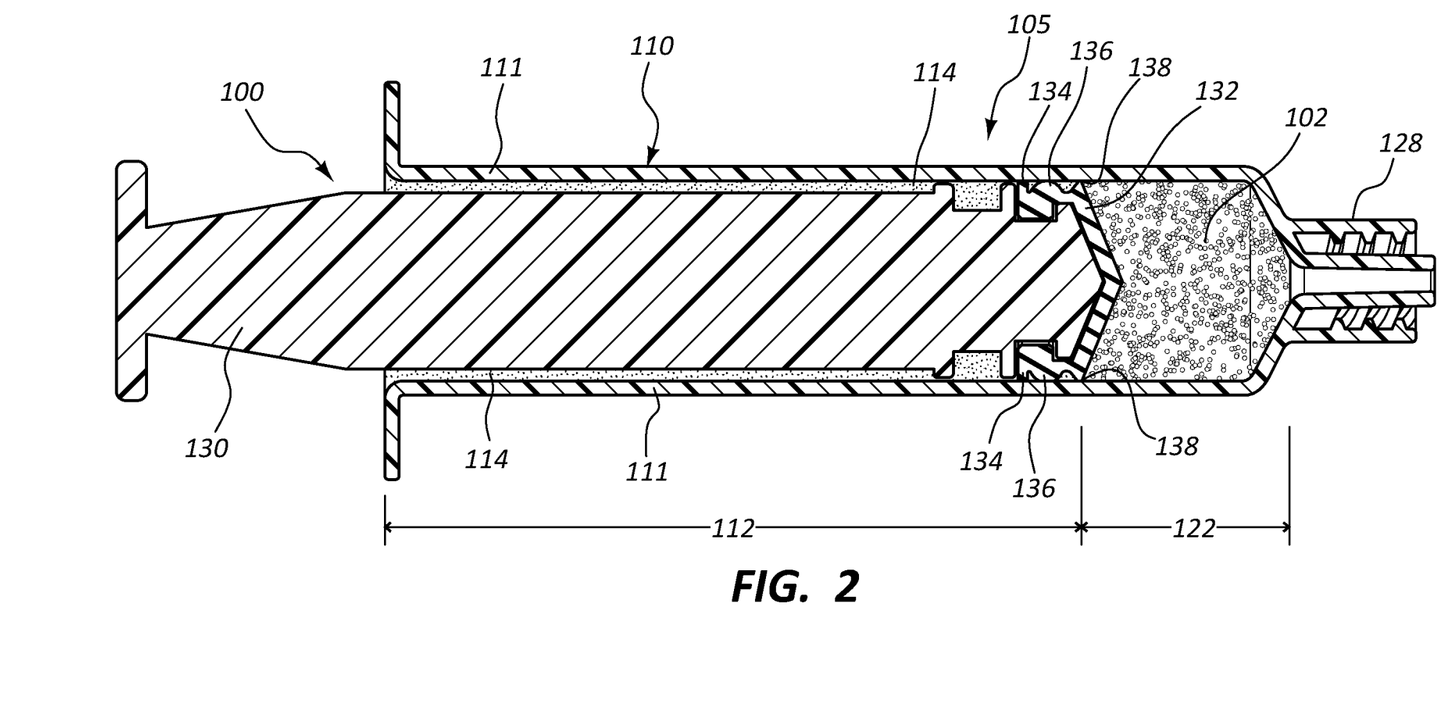
FIG. 2 is a cross-sectional side view of the syringe system of FIG. 1, wherein a non-lubricated portion of a barrel is loaded with an injectable material.
Figure 3A:
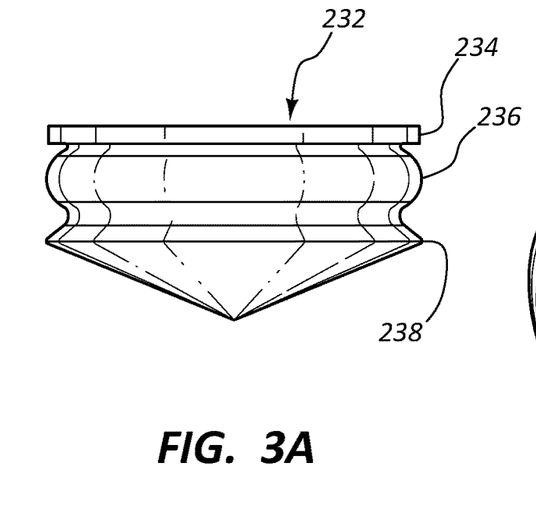
FIG. 3A is a side view of an embodiment of a seal member.
Figure 3B:
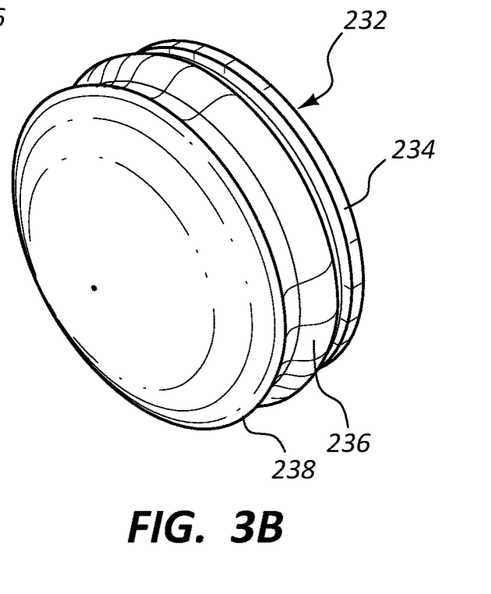
FIG. 3B is a perspective view of the seal member of FIG. 3A.
Figure 3C:
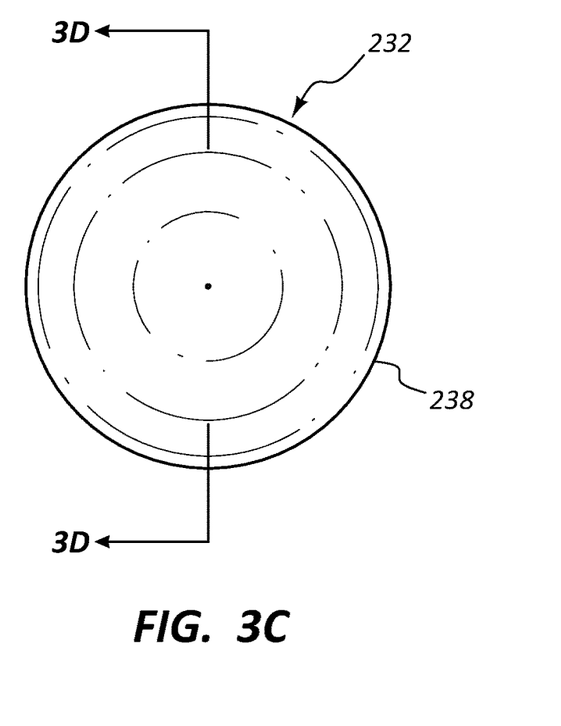
FIG. 3C is a distal end view of the seal member of FIG. 3A.
Figure 3D:
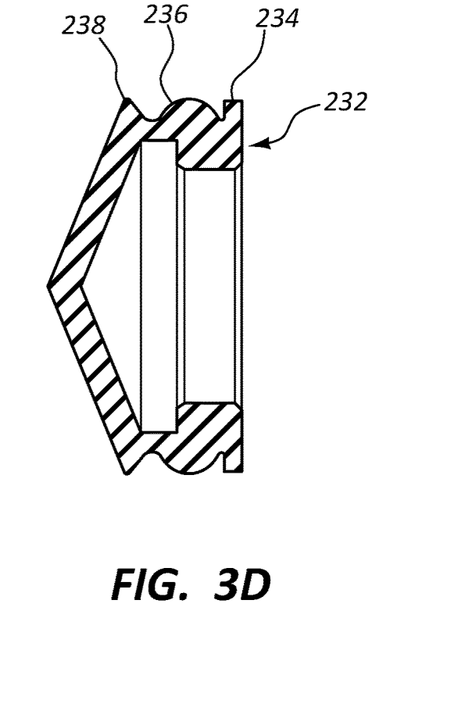
FIG. 3D is a cross-sectional view of the seal member of FIG. 3C taken through line 3D-3D.
Figure 4A:
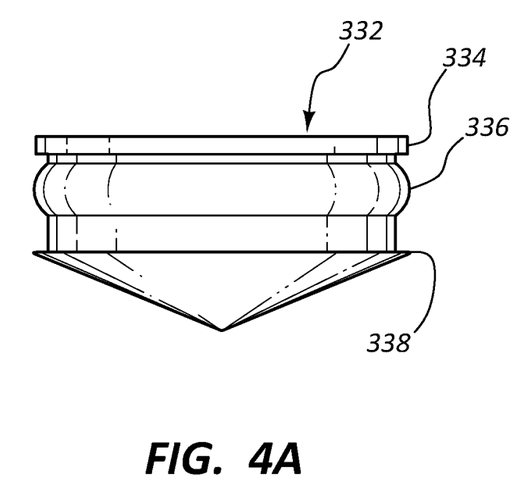
FIG. 4A is a side view of another embodiment of a seal member.
Figure 4B:
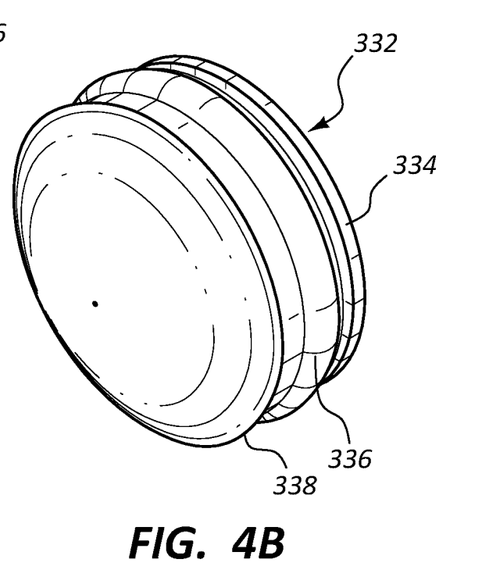
FIG. 4B is a perspective view of the seal member of FIG. 4A.
Figure 4C:
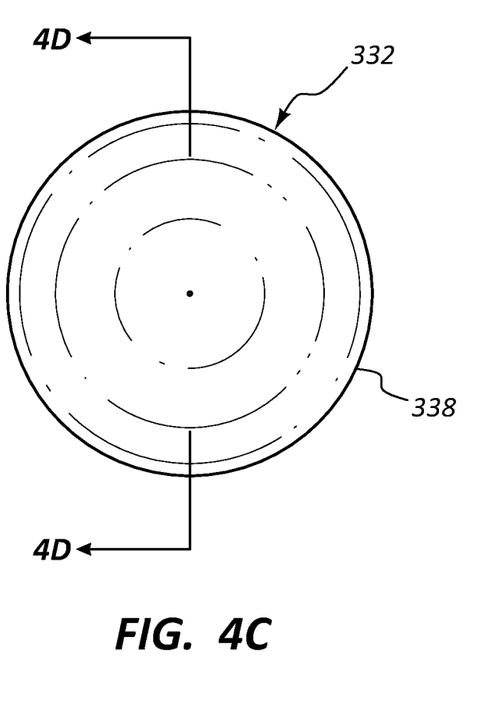
FIG. 4C is a distal end view of the seal member of FIG. 4A.
Figure 4D:
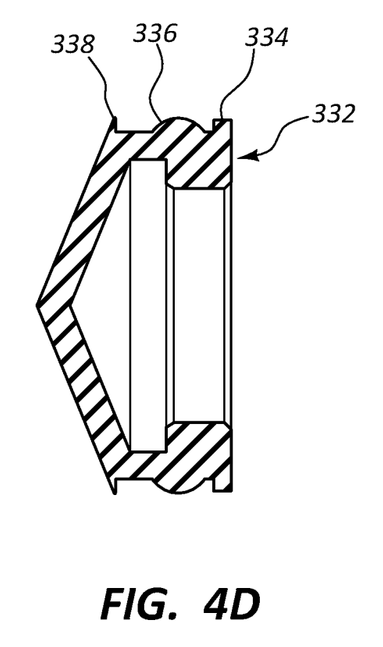
FIG. 4D is a cross-sectional view of the seal member of FIG. 4C taken through line 4D-4D.

FIG. 2 is a cross-sectional side view of the syringe system 100 of FIG. 1. As illustrated, at least a portion of the barrel 110 (i.e., the non-lubricated portion 122) may be configured to receive or be loaded with an injectable material 102. For example, the injectable material 102 may be disposed within the non-lubricated portion 122. In some embodiments, the injectable material 102 may not be compatible with the lubricant 114. For example, the injectable material 102 may be at least partially formed from a material that may become contaminated, or become unsuitable for its intended purpose, upon contact with the lubricant 114. As such, in certain embodiments, the syringe system 100 may be configured such that the injectable material 102 may be disposed in the barrel 110 such that the lubricant 114 does not, or does not substantially, come into contact with the injectable material 102 during shipment, storage, and/or sterilization. During use of the syringe system 100 (e.g., during hydration of the injectable material 102), the injectable material 102 may come into contact with the lubricant 114. In some other embodiments (i.e., wherein the lubricant 114 comprises silicone), the syringe system 100 may be configured such that the injectable material 102 does not come into contact with the lubricant 114 during use of the syringe system 100. In some such embodiments, the distal ridge 138 of the seal member 132 may inhibit, limit, or prevent the lubricant 114 from interacting with the injectable material 114. For example, upon proximal displacement of the plunger 130 and the seal member 132 during hydration of the injectable material 114, the distal ridge 138 may wipe against the interior surface of a first wall 111 of the barrel 110 and displace the lubricant 114 (e.g., the silicone lubricant or the poly-siloxane lubricant) away from the injectable material 114.

In various embodiments, the injectable material 102 may comprise PVA or be at least partially formed from PVA, while the lubricant 114 may comprise silicone or be at least partially formed from silicone. In various other embodiments, the injectable material 102 may comprise a substance including gelatin foam or be at least partially formed from a substance including gelatin foam. Disclosure of PVA herein may be analogously applied to other substances, for example, substances including gelatin foam. Materials comprising PVA or gelatin foam may become contaminated upon contact with or exposure to silicone. For example, PVA or gelatin foam may not be compatible with silicone. In various other embodiments, the lubricant 114 may comprise a non-silicone-based lubricant such as TRIBOGLIDE® (PFPE cross-linked to a surface via plasma treatment). PVA or gelatin foam may also not be compatible with the non-silicone-based lubricant. Accordingly, it may be desirable to provide a barrel 110 including both a lubricated portion 112 and a non-lubricated portion 122. The lubricated portion 112 may facilitate displacement or movement of the plunger 130 within at least a portion of the barrel 110. Additionally, the non-lubricated portion 122 may be loaded with the injectable material 102 and provide a location or position within the syringe system 100 wherein the injectable material 102 may avoid or substantially avoid contact with or exposure to the lubricant 114 (e.g., until the injectable material 102 has been hydrated).

In some embodiments, the injectable material 102 may be selected from at least one of embolic agents, polymeric microparticles, polymeric microspheres, etc. In certain embodiments, the lubricant 114 may comprise silicone. In certain other embodiments, the lubricant 114 may be a silicone-free lubricant (e.g., TRIBOGLIDE®, PFPE cross-linked to a surface via plasma treatment).

The syringe system 100 can comprise a pre-loaded syringe system. For example, as illustrated in FIG. 2, the syringe system 100 may be at least partially pre-loaded with the injection material 102. In some embodiments, the pre-loaded syringe system 100 can comprise a barrel 110, wherein at least a portion of the barrel 110 is loaded with the injection material 102 and/or the plunger 130.

In certain embodiments, the injection material 102 may be dry. In certain other embodiments, the injection material 102 may be suspended in a liquid, such as, for example, a carrier liquid comprising saline. In some embodiments, the injection material 102 may be dry during shipment and/or storage of the syringe system 100 or the barrel 110. In some other embodiments, the injection material 102 may be suspended in a liquid or hydrated during shipment and/or storage of the syringe system 100 or the barrel 110. In various embodiments, the barrel 110 or the syringe body 105 may be formed from a material selected from at least one of a polymer, a glass, and/or a metal. In various embodiments, the syringe body 105 and/or the barrel 110 may comprise a polymeric material such as, for example, a polycarbonate, a polypropylene, and/or a cyclo-olefin polymer or copolymer. Barrels 110 and/or syringe bodies 105 formed from other suitable materials are also within the scope of this disclosure.

As discussed above, the injection material 102 may be an embolic agent comprising a microparticle and/or a microsphere. Examples of microparticles include, but are not limited to, PVA microparticles (e.g., BEARING™ non-spherical PVA microparticles) and/or gelatin foam microparticles (e.g., GELFOAM® microparticles). Examples of microspheres include, but are not limited to, trisacryl cross-linked with gelatin microspheres (e.g., EMBOSPHERE® microspheres), sodium acrylate vinyl alcohol copolymer microspheres (e.g., HEPASPHERE® microspheres), PVA-based hydrogels (e.g., DC BEAD® microspheres), and/or gelatin foam microspheres (e.g., GELFOAM® microspheres).

As described above, the injection material 102 may comprise PVA or gelatin foam. In certain other embodiments, the injection material 102 may comprise an embolic agent, wherein the embolic agent may comprise PVA or gelatin foam. An injection material or an embolic agent comprising PVA may include PVA monomers, such as PVA polymers and copolymers.

In various embodiments, the pre-loaded syringe system 100 may be configured to be shelf stable for at least six months. In various other embodiments, the pre-loaded syringe system 100 may be configured to be shelf stable for at least one year, for at least two years, or for at least three years. Pre-loaded syringe systems 100 configured to be shelf stable for other suitable periods of time are also within the scope of this disclosure.

FIGS. 3A-3D are a series of views of an embodiment of a seal member 232 that can, in certain respects, resemble components of the seal member 132 described in connection with FIGS. 1 and 2. It will be appreciated that all the illustrated embodiments may have analogous features. Accordingly, like features are designated with like reference numerals, with the leading digits incremented to "2." For instance, the proximal ridge is designated as "134" in FIGS. 1 and 2, and an analogous proximal ridge 234 is designated as "234" in FIGS. 3A, 3B, and 3D. Relevant disclosure set forth above regarding similarly identified features thus may not be repeated hereafter. Moreover, specific features of the syringe system and related components (e.g., the seal member) shown in FIGS. 1 and 2 may not be shown or identified by a reference numeral in the drawings or specifically discussed in the written description that follows. However, such features may clearly be the same, or substantially the same, as features depicted in other embodiments and/or described with respect to such embodiments. Accordingly, the relevant descriptions of such features apply equally to the features of the seal member of FIGS. 3A-3D. Any suitable combination of the features, and variations of the same, described with respect to the syringe system and components illustrated in FIGS. 1 and 2 can be employed with the seal member and components of FIGS. 3A-3D, and vice versa. This pattern of disclosure applies equally to further embodiments depicted in subsequent figures and described hereafter.

As shown in FIGS. 3A-3D, the seal member 232 can comprise a proximal ridge 234, a medial ridge 236, and a distal ridge 238. The configuration and/or the shape of each of the proximal ridge 234, the medial ridge 236, and/or the distal ridge 238 may vary from the illustrated configuration or shape. As shown, the radial edge portion of the proximal ridge 234 is substantially flat, the radial edge portion of the medial ridge 236 is substantially rounded, and the radial edge portion of the distal ridge 238 is substantially tapered. Additionally, as illustrated, the radial edge portion of the distal ridge 238 extends radially of the radial edge portions of each of the proximal ridge 234 and the medial ridge 236. In some embodiments, the radial edge portions of the proximal ridge 234 and/or the medial ridge 236 may extend radially of the radial edge portion of the distal ridge 238.

The radial edge portion of the distal ridge 238 may be configured to be deformable or flexible. In some embodiments, the radial edge portion of the distal ridge 238 may be more flexible than the radial edge portions of the proximal ridge 234 and/or the medial ridge 236. In certain embodiments, the radial edge portion of the distal ridge 238 may be configured to function like a squeegee. For example, the radial edge portion of the distal ridge 238 may be configured to wipe against an interior surface of a barrel of a syringe system to control, remove, or spread a substance (e.g., a lubricant) that may be disposed on the interior surface of the barrel. As discussed above, in some embodiments, the distal ridge 238 may be configured to form a barrier seal between the seal member 232 and an interior surface of a barrel of a syringe system. The radial edge portions of the proximal ridge 234 and/or the medial ridge 236, however, may be less deformable or flexible than the radial edge portion of the distal ridge 238. As discussed above, in some embodiments, the proximal ridge 234 and/or the medial ridge 236 may be configured to form a pressure seal between the seal member 232 and an interior surface of a barrel of a syringe system.

FIGS. 4A-4D are a series of views of another embodiment of a seal member 332. Analogous to the seal member 232 (see FIGS. 3A-3D), the seal member 332 comprises a proximal ridge 334, a medial ridge 336, and a distal ridge 338. In comparison to the radial edge portion of the distal ridge 238 of the seal member 232, a radial edge portion of the distal ridge 338 is narrower or thinner. As such, the distal ridge 338 may be more deformable or flexible than the distal ridge 238. In some embodiments, the flexibility of the distal ridge 338 may be adjusted based on various factors. For example, the flexibility of the distal ridge 338 may be adjusted based on a viscosity of a lubricant that is disposed in a barrel of a syringe system.

Figure 5:
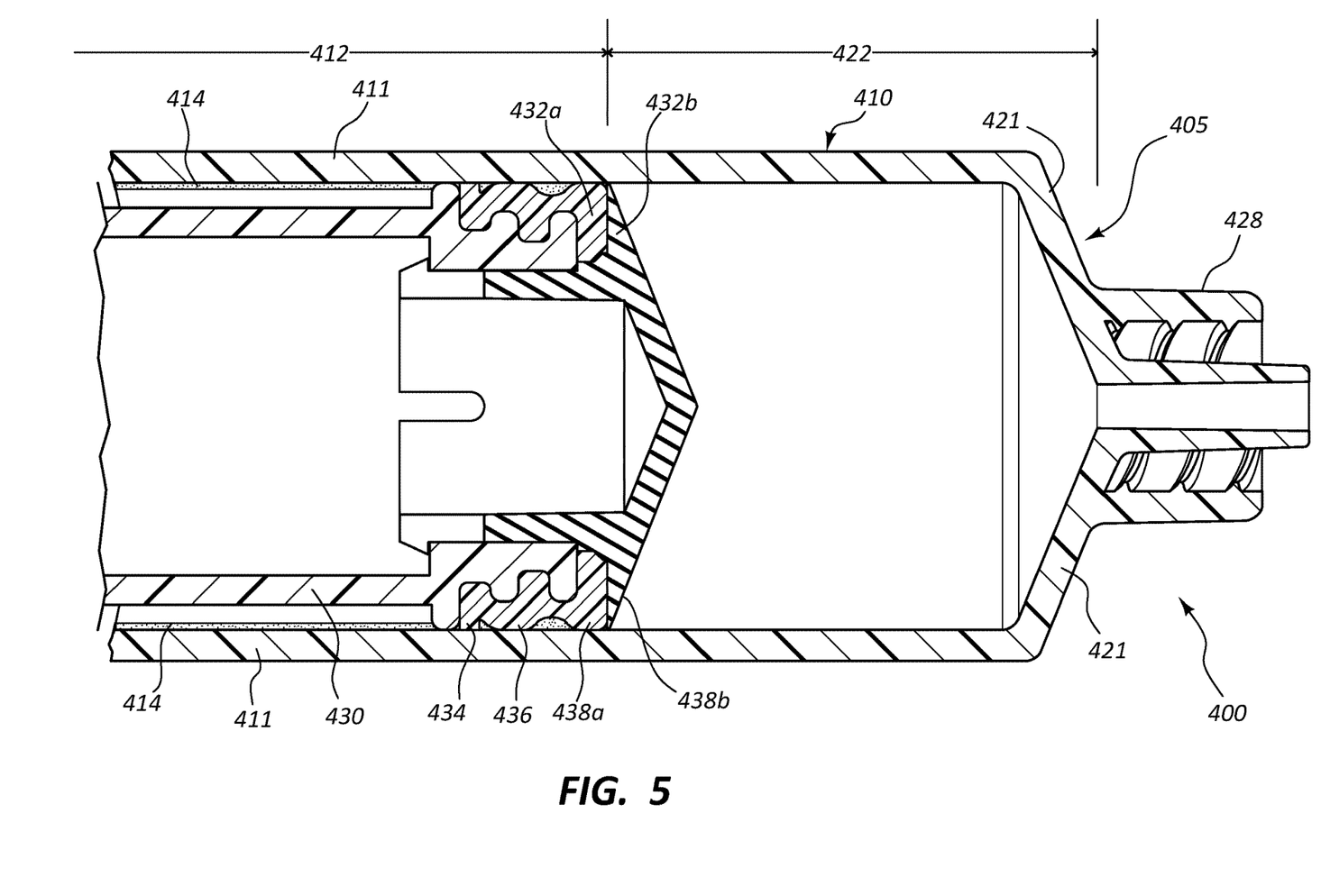
FIG. 5 is a side cross-sectional view of a portion of another embodiment of a syringe system.
Figure 6A:
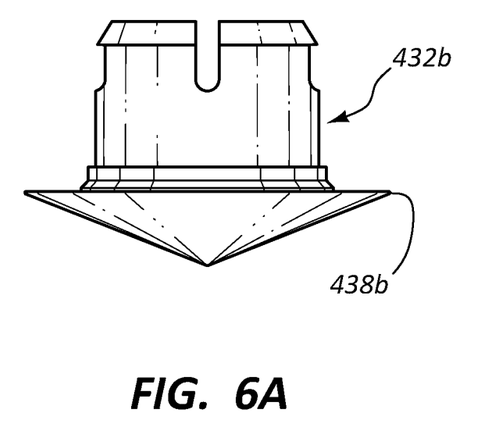
FIG. 6A is a side view of a distal seal member portion of the syringe system of FIG. 5.
Figure 6B:
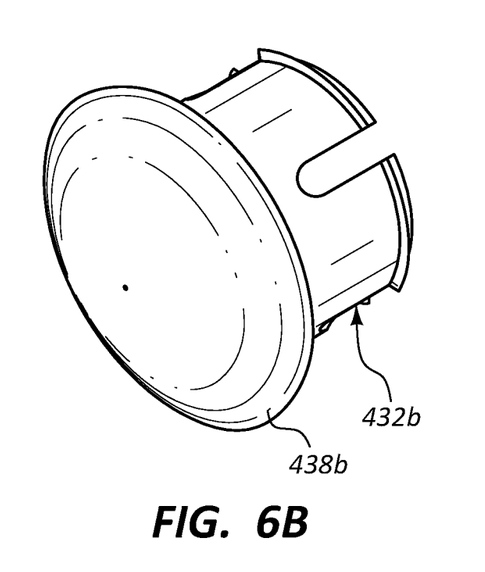
FIG. 6B is a perspective view of the distal seal member portion of FIG. 6A.
Figure 6C:
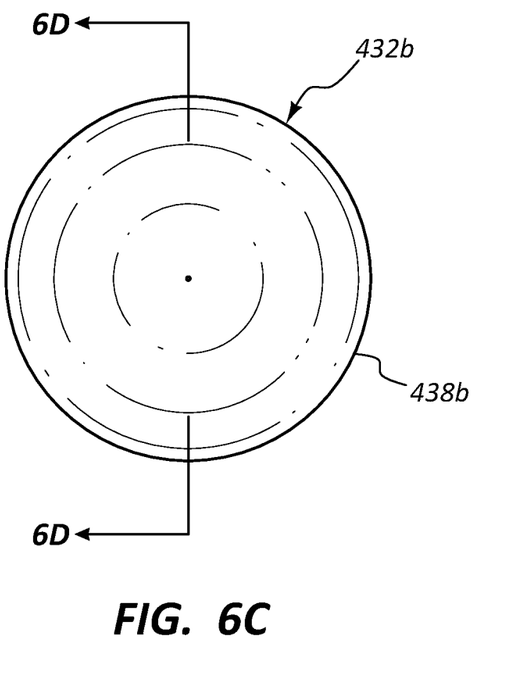
FIG. 6C is a distal end view of the distal seal member portion of FIG. 6A.
Figure 6D:
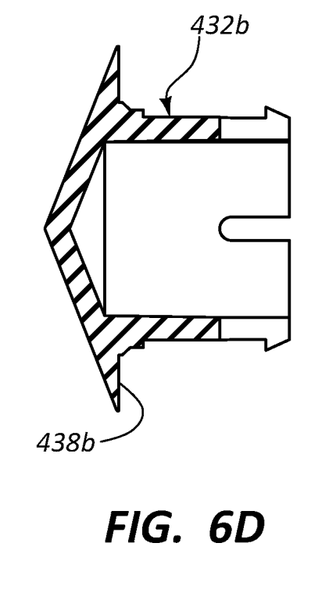
FIG. 6D is a cross-sectional view of the distal seal member portion of FIG. 6C taken through line 6D-6D.

FIG. 5 is a cross-sectional side view of a portion of a syringe system 400. As illustrated, the syringe system 400 comprises a first wall 411, wherein the first wall 411 at least partially defines a barrel 410 of a syringe body 405. The barrel 410 is configured to receive a plunger 430. The syringe body 405 also comprises a second wall 421, wherein the second wall 421 is disposed at a distal end of the barrel 410. As depicted, an inlet/outlet port or port 428 can be disposed in at least a portion of the second wall 421.

As shown, the barrel 410 can comprise a proximal or lubricated portion 412, wherein at least a portion of an interior surface of the first wall 411 of the proximal portion 412 is coated with a lubricant 414. Furthermore, the barrel 410 can comprise a distal or non-lubricated portion 422, wherein at least a portion of an interior surface of the first wall 411 of the distal portion 422 is not coated with a lubricant (i.e., the distal portion 422 is not lubricated).

As depicted, the plunger 430 can comprise a seal member, the seal member comprising a proximal seal member portion 432a and a distal seal member portion 432b. The distal seal member portion 432b can be configured to be disposed within and/or coupleable to an interior portion of a distal end of the plunger 430. As shown, the distal seal member portion 432b can further comprise a distal ridge 438b. In some embodiments, the distal ridge 438b may be configured to contact and/or wipe against an interior surface of the first wall 411. The distal ridge 438b may form a barrier seal between the distal seal member portion 432b and the interior surface of the first wall 411. The proximal seal member portion 432a can be configured to be disposed around and/or coupleable to an exterior portion of the distal end of the plunger 430. As shown, the proximal seal member portion 432b can further comprise a proximal ridge 434, a medial ridge 436, and a distal ridge 438a. In some embodiments, the proximal ridge 434, the medial ridge 436, and the distal ridge 438a can be configured to form a pressure seal between the proximal seal member portion 432a and the interior surface of the first wall 411. Furthermore, the proximal seal member portion 432a may be configured to be coupled to the distal seal member portion 432b, or vice versa.

FIGS. 6A-6D are a series of views of the distal seal member portion 432b. As shown, the distal seal member portion 432b comprises a distal ridge 438b. A radial edge portion of the distal ridge 438b is substantially tapered (e.g., tapers to a point) and, in some embodiments, at least a portion of the distal ridge 438b may be deformable or flexible. Accordingly, as discussed above, the distal ridge 438b may be configured to wipe against at least a portion of the interior surface of the first wall 411. Stated another way, the distal ridge 438b may be configured to function in a manner analogous to a squeegee.

Figure 7:
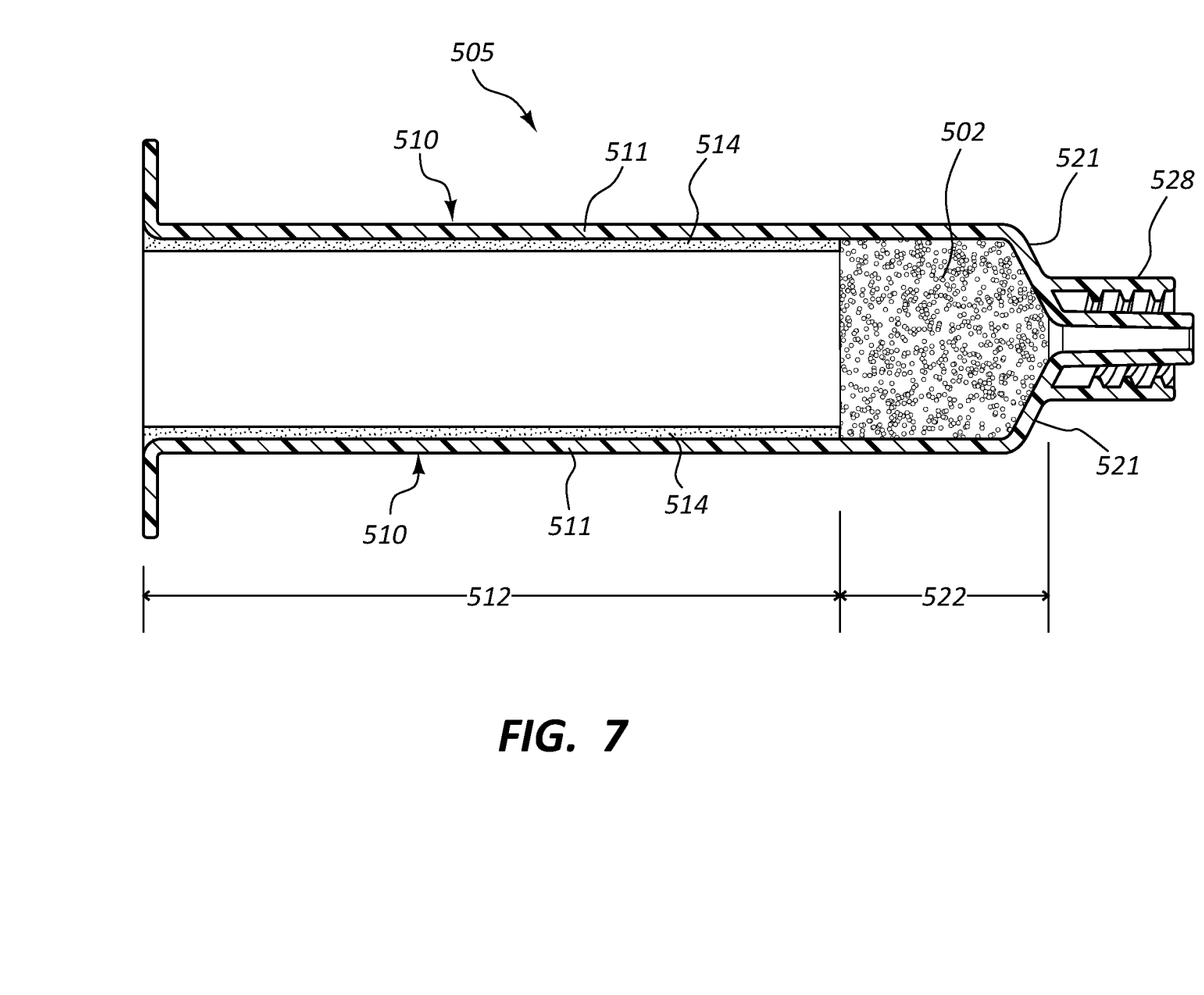
FIG. 7 is a cross-sectional side view of an embodiment of a syringe body.

FIG. 7 is a cross-sectional side view of a syringe body 505. As depicted, a first wall 511 can define a barrel 510 (e.g., a substantially cylindrical barrel 510), wherein the barrel 510 is configured to receive a plunger (not shown). Furthermore, a second wall 521 (e.g., a substantially frustoconical second wall 521) can be coupled to or integral with the first wall 511 at a distal end of the barrel 510. Stated another way, the second wall 521 can form at least a portion of the distal end of the barrel 510. The syringe body 505 can also include an inlet/outlet port 528 that is disposed in at least a portion of the second wall 521. As discussed above, the barrel 510 can comprise a proximal or lubricated portion 512 that is at least partially coated with a lubricant 514. The barrel 510 can further comprise a distal or non-lubricated portion 522 that is not coated with a lubricant or that is lubricant-free. The non-lubricated portion 522 of the barrel 510 can be configured to receive an injectable material 502 or may be loaded (e.g., pre-loaded) with the injectable material 502.

In some embodiments, the syringe system (e.g., syringe systems 100, 400, 500) and components thereof may comprise sterilization compatible materials. In certain embodiments, the syringe systems and components thereof may comprise irradiation compatible materials.

Kits comprising syringe systems or syringe bodies at least partially pre-loaded with an injectable material are disclosed herein. In some embodiments, the pre-loaded syringe system may comprise a barrel at least partially loaded with the injection material and a plunger in communication with an interior surface of the barrel. In some other embodiments, the pre-loaded syringe body may comprise a barrel at least partially loaded with the injection material.

In certain embodiments, the injection material of the kit may be dry. In certain other embodiments, the injection material of the kit may be suspended in a liquid such as, but not limited to, a carrier liquid comprising saline. In various embodiments, the syringe body and/or the barrel may be formed from a material selected from at least one of a polymer, a glass, and/or a metal. As stated above, syringe bodies and/or barrels formed from other suitable materials are also within the scope of this disclosure.

In some embodiments, the kit and/or the components of the kit may be configured to be shelf stable for at least six months, for at least one year, for at least two years, for at least three years, or for another suitable period of time. In certain embodiments, the syringe system or syringe body of the kit may comprise sterilization compatible materials and/or irradiation compatible materials.

Figure 8A:
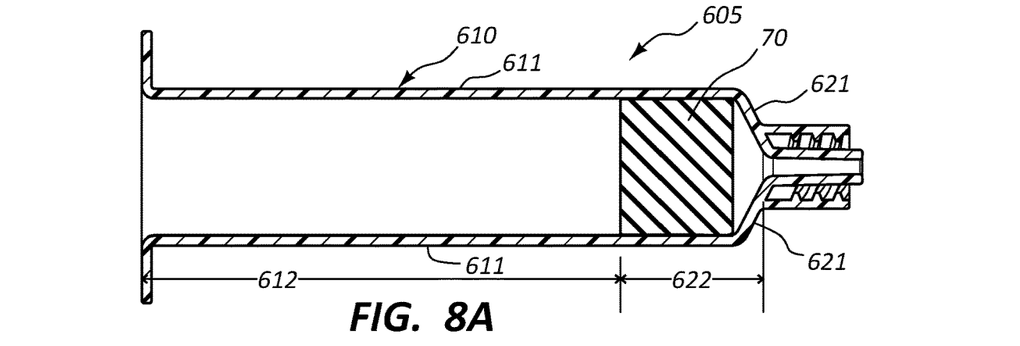
FIG. 8A is a cross-sectional side view of another embodiment of a syringe body, wherein a spacer is disposed in the syringe body.

Methods of lubricating a portion of an interior surface of a syringe barrel are also disclosed herein. FIGS. 8A-8D depict an embodiment of a method of lubricating a portion of the interior surface of a syringe barrel 610. In some embodiments, the methods may comprise obtaining a syringe body 605. As depicted in FIG. 8A, the methods may further comprise inserting or disposing a spacer or puck 70 into at least a portion of the syringe barrel 610. The methods may also comprise disposing the spacer 70 at or adjacent a distal or second wall 621 of the syringe body 605.

Figure 8B:
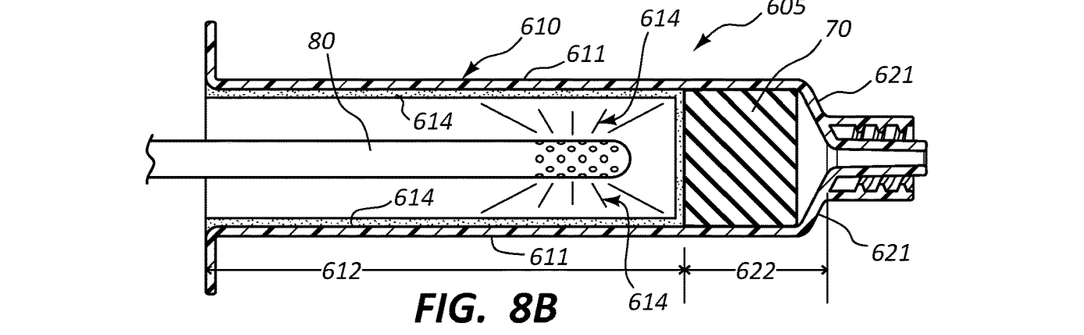
FIG. 8B is a cross-sectional side view of the syringe body of FIG. 8A, wherein a lubricant is being applied to a portion of an interior surface of a first wall of a barrel of the syringe body.
Figure 8C:
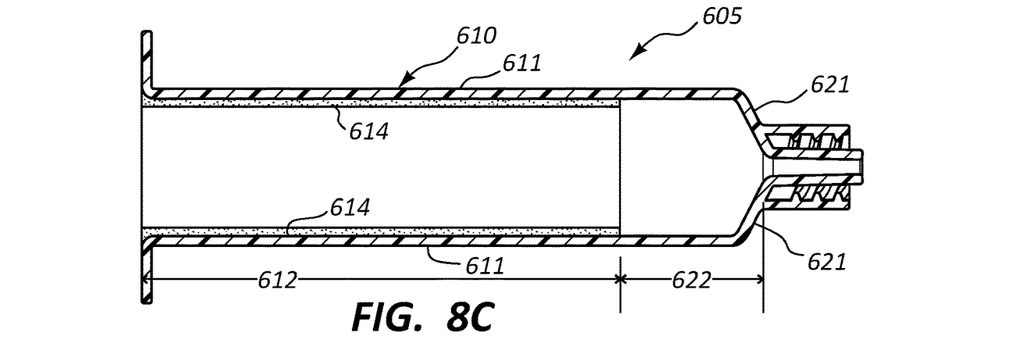
FIG. 8C is a cross-sectional side view of the syringe body of FIG. 8A, wherein the lubricant has been applied and the spacer has been removed.

In certain embodiments, the methods may also comprise applying a lubricant on at least a portion of an interior surface of a portion of a first wall 611 of the syringe body 605. As shown in FIG. 8B, a lubricant applicator 80 may be used to apply the lubricant 614 to the interior surface of a portion of a first wall 611 of the syringe barrel 610. Other suitable methods of applying the lubricant 614 are also within the scope of this disclosure. For example, the lubricant 614 may be applied by dipping, swabbing, etc. As depicted, the spacer 70 may be configured to inhibit, limit, or prevent exposure of a portion of the interior surface of the first wall 611. For example, the spacer 70 may inhibit, limit, or prevent application of the lubricant 614 to a distal or non-lubricated portion 622 of the syringe barrel 610. The methods may also comprise, adhering, cross-linking, or curing the applied lubricant 614, i.e., to the interior surface of a portion of the first wall 611 of the syringe barrel 610. The methods may further comprise, as depicted in FIG. 8C, removing or retrieving the spacer 70 from the syringe barrel 610, which may expose the non-lubricated portion 622 of the syringe barrel 610.

Figure 8D:
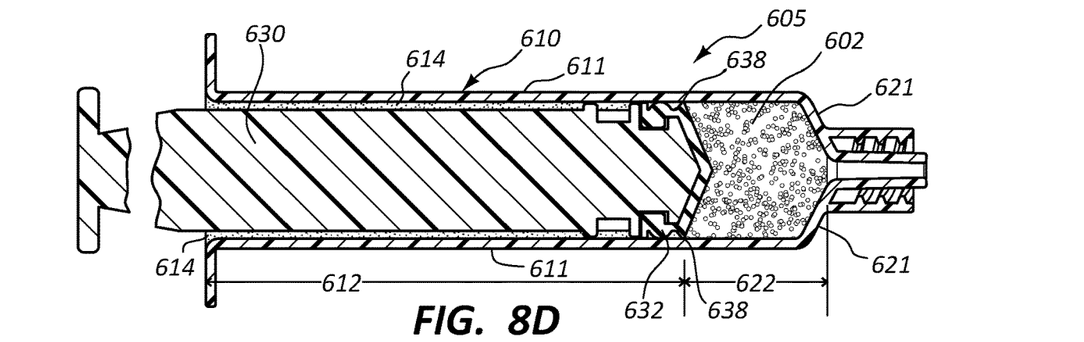
FIG. 8D is a cross-sectional side view of the syringe body of FIG. 8A, wherein a non-lubricated portion of the barrel has been loaded with an injectable material and wherein a plunger has been disposed in the barrel.

As depicted in FIG. 8D, the methods may also comprise disposing an injectable material 602 within at least a portion of the non-lubricated portion 622 of the syringe barrel 610. Further, the methods may comprise inserting a plunger 630 including a seal member 632 within at least a portion of the syringe barrel 610. The plunger 630 may also be displaced within the syringe barrel 610 such that a distal ridge 638 of the seal member 632 is disposed between each of a proximal or lubricated portion 612 and the distal or non-lubricated portion 622 of the syringe barrel 610.

In some other embodiments, methods of lubricating an interior surface of a syringe barrel may comprise obtaining a plunger, wherein the plunger comprises a seal member. As discussed above, the seal member may include a proximal ridge disposed around a circumference of the seal member. In certain embodiments, the seal member may further comprise a distal ridge disposed around the circumference of the seal member at a position distal of the proximal ridge.

In contrast to methods comprising the spacer 70 and/or adhering the applied lubricant 614, methods of lubricating the interior surface of the syringe barrel may comprise applying a lubricant to at least a portion of an exterior surface of the seal member. In various embodiments, the lubricant may be applied to a proximal ridge of the seal. In various other embodiments, the seal member may further comprise a medial ridge disposed between each of the proximal ridge and the distal ridge of the seal member. In some methods, the lubricant may be applied to each of the proximal ridge and the medial ridge of the seal member. The plunger comprising the lubricated seal member may then be disposed within at least a proximal portion of the syringe barrel and the plunger may be displaced toward a distal portion of the syringe barrel such that at least a portion of an interior surface of the proximal portion of the syringe barrel is coated with the lubricant, i.e., forming a lubricated portion of the syringe barrel.

In some embodiments, the methods may further comprise stopping the displacement of the plunger and the seal member such that an interior surface of the distal portion of the syringe barrel is not coated with the lubricant, i.e., forming a non-lubricated portion of the syringe barrel. Stated another way, the displacement of the plunger may be halted such that the distal portion of the syringe barrel remains uncoated (i.e., the distal portion of the syringe barrel may be a non-lubricated portion). In some other embodiments, an injectable material may be disposed or loaded in at least a portion of the syringe barrel (e.g., the distal portion) prior to lubricating the syringe barrel. In some embodiments, the methods may further comprise keeping the interior surface of the distal portion of the syringe barrel and/or a distal surface of the seal member substantially free from the lubricant. As can be appreciated, additional methods and/or method steps can be derived from FIGS. 1-8D and the corresponding disclosure.

In yet some other embodiments, methods of separating an injectable material from a contaminant are also disclosed herein. In certain embodiments, the injectable material may comprise PVA or gelatin foam. As discussed above, some injectable materials (e.g., some injectable materials comprising PVA or gelatin foam) may become contaminated by contact with or exposure to a lubricant. Specifically, lubricants comprising silicone and/or silicone-free lubricants such as TRIBOGLIDE® (PFPE cross-linked to a surface via plasma treatment) may contaminate the injectable material (e.g., PVA-comprising injectable materials or gelatin foam-comprising injectable materials).

Methods of separating the injectable material from the lubricant may comprise lubricating a proximal portion of a syringe barrel of a syringe body and not lubricating a distal portion of the syringe barrel. The methods may further comprise disposing or loading the injectable material in the distal or non-lubricated portion of the syringe barrel. Additionally, the methods may comprise disposing a plunger including a seal member within at least a portion of the syringe barrel such that a ridge (e.g., a distal ridge, as discussed above) is disposed between each of the lubricated portion and the non-lubricated portion of the syringe barrel. The seal member may inhibit, limit, or prevent flow or migration of the lubricant from the lubricated portion to the non-lubricated portion of the syringe barrel such that the injectable material, which is disposed in the non-lubricated portion, is not contaminated by the lubricant (i.e., by contact with or exposure to the lubricant). Analogously, the seal member may inhibit, limit, or prevent flow or migration of the injectable material from the non-lubricated portion to the lubricated portion of the syringe barrel such that the injectable material is not contaminated by the lubricant (i.e., by contact with or exposure to the lubricant).

Any methods disclosed herein comprise one or more steps or actions for performing the described method. The method steps and/or actions may be interchanged with one another. In other words, unless a specific order of steps or actions is required for proper operation of the embodiment, the order and/or use of specific steps and/or actions may be modified.

References to approximations are made throughout this specification, such as by use of the term "substantially." For each such reference, it is to be understood that, in some embodiments, the value, feature, or characteristic may be specified without approximation. For example, where qualifiers such as "about" and "substantially" are used, these terms include within their scope the qualified words in the absence of their qualifiers. For example, where the term "substantially aligned" is recited with respect to a feature, it is understood that in further embodiments, the feature can have a precisely aligned configuration.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

Without further elaboration, it is believed that one skilled in the art can use the preceding description to utilize the invention to its fullest extent. The claims and embodiments disclosed herein are to be construed as merely illustrative and exemplary, and not a limitation of the scope of the present disclosure in any way. It will be apparent to those having ordinary skill in the art, with the aid of the present disclosure, that changes may be made to the details of the above-described embodiments without departing from the underlying principles of the disclosure herein. In other words, various modifications and improvements of the embodiments specifically disclosed in the description above are within the scope of the appended claims. Moreover, the order of the steps or actions of the methods disclosed herein may be changed by those skilled in the art without departing from the scope of the present disclosure. In other words, unless a specific order of steps or actions is required for proper operation of the embodiment, the order or use of specific steps or actions may be modified. The scope of the invention is therefore defined by the following claims and their equivalents.

The invention claimed is:

1. A syringe system, comprising:
a barrel comprising:

a lubricated portion;
a non-lubricated portion disposed distal of the lubricated portion; and
a plunger configured to be disposed within the barrel,
wherein the plunger comprises a seal member, the seal member including a proximal ridge disposed around a circumference of the seal member and a distal ridge disposed around the circumference of the seal member at a position distal of the proximal ridge,
wherein the distal ridge comprises a radial edge portion that extends radially of a radial edge portion of the proximal ridge,
wherein the radial edge portion of the distal ridge comprises a tapered portion configured to wipe against the interior surface of the first wall, and
wherein the radial edge portion of the distal ridge comprises a distal tapered surface and a proximal tapered surface converging to form a radial corner.

2. The syringe system of claim 1, wherein the distal ridge is configured to inhibit migration of a lubricant from the lubricated portion to the non-lubricated portion.

3. The syringe system of claim 1, wherein each of the proximal ridge and the distal ridge exerts a radial force on an interior surface of a first wall of the barrel, and wherein the radial force of the proximal ridge is greater than the radial force of the distal ridge.

4. The syringe system of claim 3, wherein the seal member further comprises a medial ridge disposed between the proximal ridge and the distal ridge, wherein the medial ridge exerts a radial force on the interior surface of the first wall of the barrel, and wherein the radial force of the medial ridge is greater than the radial force of the distal ridge.

5. The syringe system of claim 1, wherein an interior surface of a first wall of the barrel of the lubricated portion comprises a lubricant coating, and wherein an interior surface of the first wall of the barrel of the non-lubricated portion lacks a lubricant coating.

6. The syringe system of claim 5, wherein the lubricant coating comprises silicone.

7. The syringe system of claim 5, wherein the lubricant coating is a silicone-free lubricant.

8. The syringe system of claim 5, wherein the lubricant coating is adhered to the interior surface of the first wall of the barrel of the lubricated portion.

9. A syringe system, comprising:
a first wall defining a barrel configured to receive a plunger, the barrel comprising:
a proximal portion, wherein an interior surface of the first wall of the proximal portion is coated with a lubricant; and
a distal portion, wherein an interior surface of the first wall of the distal portion is not coated with the lubricant;
a second wall disposed at a distal end of the barrel, the second wall comprising a port disposed in the second wall, wherein an interior surface of the second wall is not coated with the lubricant; and
an injectable material disposed within the distal portion, the injectable material positioned such that the plunger defines a barrier between the injectable material and the lubricant when the syringe system is in a storage configuration,
wherein the plunger comprises a seal member, the seal member including a proximal ridge disposed around a circumference of the seal member and a distal ridge disposed around the circumference of the seal member at a position distal of the proximal ridge,
wherein the distal ridge comprises a radial edge portion that extends radially of a radial edge portion of the proximal ridge,
wherein the radial edge portion of the distal ridge comprises a tapered portion configured to wipe against the interior surface of the first wall, and
wherein the radial edge portion of the distal ridge comprises a distal tapered surface and a proximal tapered surface converging to form a sharp radial tip.

10. The syringe body of claim 9, wherein the lubricant is a silicone-free lubricant.

11. The syringe body of claim 9, wherein the injectable material comprises polyvinyl alcohol.

12. A syringe body, comprising:
a first wall defining a barrel configured to receive a plunger, the barrel comprising:
a proximal portion, wherein an interior surface of the first wall of the proximal portion is coated with a lubricant;
a distal portion, wherein an interior surface of the first wall of the distal portion is not coated with the lubricant; and
a second wall disposed at a distal end of the barrel, the second wall comprising a port disposed in the second wall, wherein an interior surface of the second wall is not coated with the lubricant, wherein
the distal portion and plunger are configured to define a storage zone,
the storage zone is configured to receive an entire storage volume of an injectable material,
the storage zone is positioned distal of the lubricant such that contact between the injectable material and the lubricant is prevented during storage,
wherein the plunger comprises a seal member, the seal member including a proximal ridge disposed around a circumference of the seal member and a distal ridge disposed around the circumference of the seal member at a position distal of the proximal ridge,
wherein the distal ridge comprises a radial edge portion that extends radially of a radial edge portion of the proximal ridge,
wherein the radial edge portion of the distal ridge comprises a tapered portion configured to wipe against the interior surface of the first wall, and
wherein the radial edge portion of the distal ridge comprises a substantially triangular shape with a distal tapered surface and a proximal tapered surface converging to form an apex.

* * * * *

UNITED STATES PATENT AND TRADEMARK OFFICE
CERTIFICATE OF CORRECTION

PATENT NO. : 10,737,033 B2
APPLICATION NO. : 15/410364
DATED : August 11, 2020
INVENTOR(S) : Butts et al.

Page 1 of 1

It is certified that error appears in the above-identified patent and that said Letters Patent is hereby corrected as shown below:

In the Claims

Column 13, Line 15 Claim 1, reads, ". . . of the first wall, . . ." which should read, "… of a first wall, . . ."

Column 14, Line 20 Claim 10, reads, "The syringe body of claim 9 . . ." which should read, "The syringe system of claim 9 . . ."

Column 14, Line 22 Claim 11, reads, "The syringe body of claim 9 . . ." which should read, "The syringe system of claim 9 . . ."

Signed and Sealed this
Twenty-fourth Day of September, 2024

Katherine Kelly Vidal
*Director of the United States Patent and Trademark Office*